United States Patent [19]
Herbst

[11] Patent Number: 5,876,364
[45] Date of Patent: Mar. 2, 1999

[54] ORTHOTIC CUSHIONED ARTICLE TO PREVENT FOOT AND ANKLE DECUBITAL ULCERS

[76] Inventor: R. Jamey Herbst, 923 Ohio Pike, Cincinnati, Ohio 45245

[21] Appl. No.: 114,405

[22] Filed: Jul. 13, 1998

[51] Int. Cl.[6] .................................................... A61F 5/00
[52] U.S. Cl. ............................................. 602/27; 602/13
[58] Field of Search .................................. 602/5, 13, 23, 602/27–29, 61–62, 65; 128/882, 892; 5/649–651

[56] References Cited

U.S. PATENT DOCUMENTS

| | | |
|---|---|---|
| Re. 30,444 | 12/1980 | Spann . |
| 3,745,998 | 7/1973 | Rose . |
| 4,263,905 | 4/1981 | Couch, Jr. . |
| 4,657,003 | 4/1987 | Wirtz . |
| 4,862,879 | 9/1989 | Coombs . |
| 4,885,811 | 12/1989 | Hayes . |
| 5,226,245 | 7/1993 | Lamont .............................. 128/892 X |
| 5,489,259 | 2/1996 | Jacobs et al. ............................ 602/13 |
| 5,609,570 | 3/1997 | Lamont ..................................... 602/65 |
| 5,762,622 | 6/1998 | Lamont ..................................... 602/65 |

*Primary Examiner*—Linda C. M. Dvorak
*Attorney, Agent, or Firm*—Charles R. Wilson

[57] ABSTRACT

An orthotic cushioned article is for use by bed-ridden individuals to prop a foot off a bed or other abrasive surface. The article is generally L-shaped with a leg portion and a foot portion. The leg portion has a flattened centerwall with upwardly extending sidewalls. Each of the sidewalls has a cut-out to accommodate the individual's ankle bones. The leg portion and foot portion form a junction where they meet and that junction has a cut-out to accommodate the individual's heel bone. The cushioned article also has securing means to hold it to the individual's lower leg and foot. It further has beads in at least the centerwall of the leg portion to enhance blood circulation. The orthotic cushioned article effectively prevents the formation of decubital ulcers in the individual's leg and foot.

16 Claims, 5 Drawing Sheets

5,876,364

ORTHOTIC CUSHIONED ARTICLE TO PREVENT FOOT AND ANKLE DECUBITAL ULCERS

FIELD OF INVENTION

This invention relates to an orthotic cushioned article. More particularly, the invention relates to an orthotic cushioned article for supporting the foot and ankle of an individual in a manner to prevent the formation of decubital ulcers.

BACKGROUND OF INVENTION

Individuals become bed-ridden for several different reasons. A person may be bed-ridden for a temporary time period while healing from an accident or illness. A person may also be bed-ridden for a more prolonged time period or even a time period of indefinite duration because of a serious illness. In either case, care must be taken to prevent the formation of decubital ulcers, commonly referred to as pressure sores or bed sores. The ulcers tend to form on bony areas of the body which make constant or near constant contact with a bed surface. For example, an individual's heels, ankles, and elbows are bony areas with a minimal amount of fleshy protective covering.

The heel and ankle of a bed-ridden individual in particular are susceptible to the formation of decubital ulcers. The individual lying on his back or side will cause the heels and ankles to be in constant contact with a bed surface. Natural foot movements of such an individual over time only aggravate the situation.

Decubital ulcers have been a source of discomfort to many people. Once formed, they are hard to heal. Various ointments and salves have been developed specifically for decubital ulcers. Various foot prop articles designed to prevent the formation of the ulcers or at least alleviate the discomfort associated with the ulcers have also been developed. Most of the known articles have varied means to suspend the foot of a bed-ridden individual off a bed surface. U.S. Pat. Nos. 3,511,233, 4,076,022, 4,197,845, 4,266,298, 4,409,975, 5,085,214, 5,328,445 and 5,449,339 all contain descriptions of products which were designed to suspend a heel off a hard or abrasive surface. None of the disclosed products meet all the needs of a anti-decubital ulcer product which is economical to produce, easy to use, cleanable for reuse and, most importantly, effective for its intended use.

There has now been developed an orthotic cushioned article for use by bed-ridden individuals. The article prevents the formation of decubital ulcers in the heel and ankles of individuals. It is economical to produce. It is easy to clean. If effectively prevents and alleviates discomfort often times experienced by many bed-ridden individuals.

SUMMARY OF INVENTION

An orthotic cushioned article is designed to hold an individual's foot and ankle in an inclined position and in a manner which alleviates or prevents decubital ulcers. The cushioned article is generally L-shaped to follow the contour of the individual's lower leg and foot. It has a leg portion and a foot portion. The leg portion has a flattened centerwall and upwardly extending first and second sidewalls. Each of the sidewalls has a cut-out to accommodate the individual's ankle bone. The foot portion also has a flattened centerwall. Another cut-out to accommodate the individual's heel is formed in the cushioned article at a junction of the leg portion and foot portion. Beads in the cushioned article in at least the centerwall of the leg portion enhance blood circulation and preferably sorb odors. The cushioned article also has securing means to releasably hold it to the individual for an extended recuperative time period. The orthotic cushioned article provides support for the individual's foot and ankle without causing decubital ulcer aggravation or formation.

DETAILED DESCRIPTION OF INVENTION

An orthotic cushioned article of the invention is described in detail in the following paragraphs and with reference to the drawings. The article described is for use by an individual on either the left or right lower leg and foot. It can be sized in a routine manner to fit a young child or a full grown adult.

Figure 1:
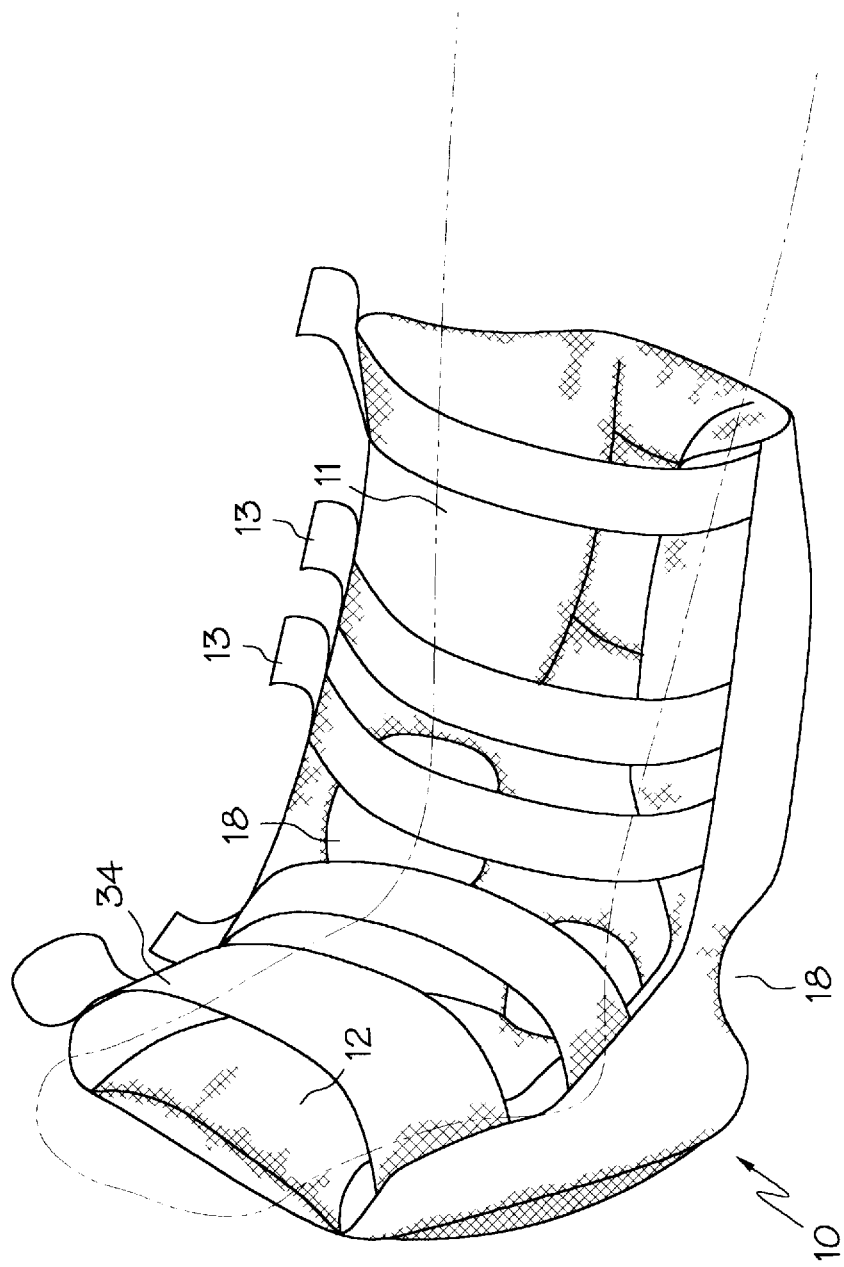
FIG. 1 is an environmental view of the orthotic cushioned article of the invention.

With reference to FIG. 1, the orthotic cushioned article 10 is positioned on a lower leg and foot (shown in phantom) of an individual who is lying in an inclined position. The article is intended for use by an individual who is restricted to the inclined position and normally confined to a bed. It is not intended for use by an ambulatory individual. The cushioned article has a generally L-shaped configuration with a leg portion 11 and a foot portion 12. It also has securing means 13 in the form of straps to semi-permanently hold the cushioned article to the leg and foot of the individual. While not evident in FIG. 1, the orthotic cushioned article 10 also has a set of beads in at least the leg portion 11 of the article below a covering surface to enhance blood circulation and preferably to sorb odors. Each of the components of the cushioned article is described in detail in the following paragraphs.

Figure 2:
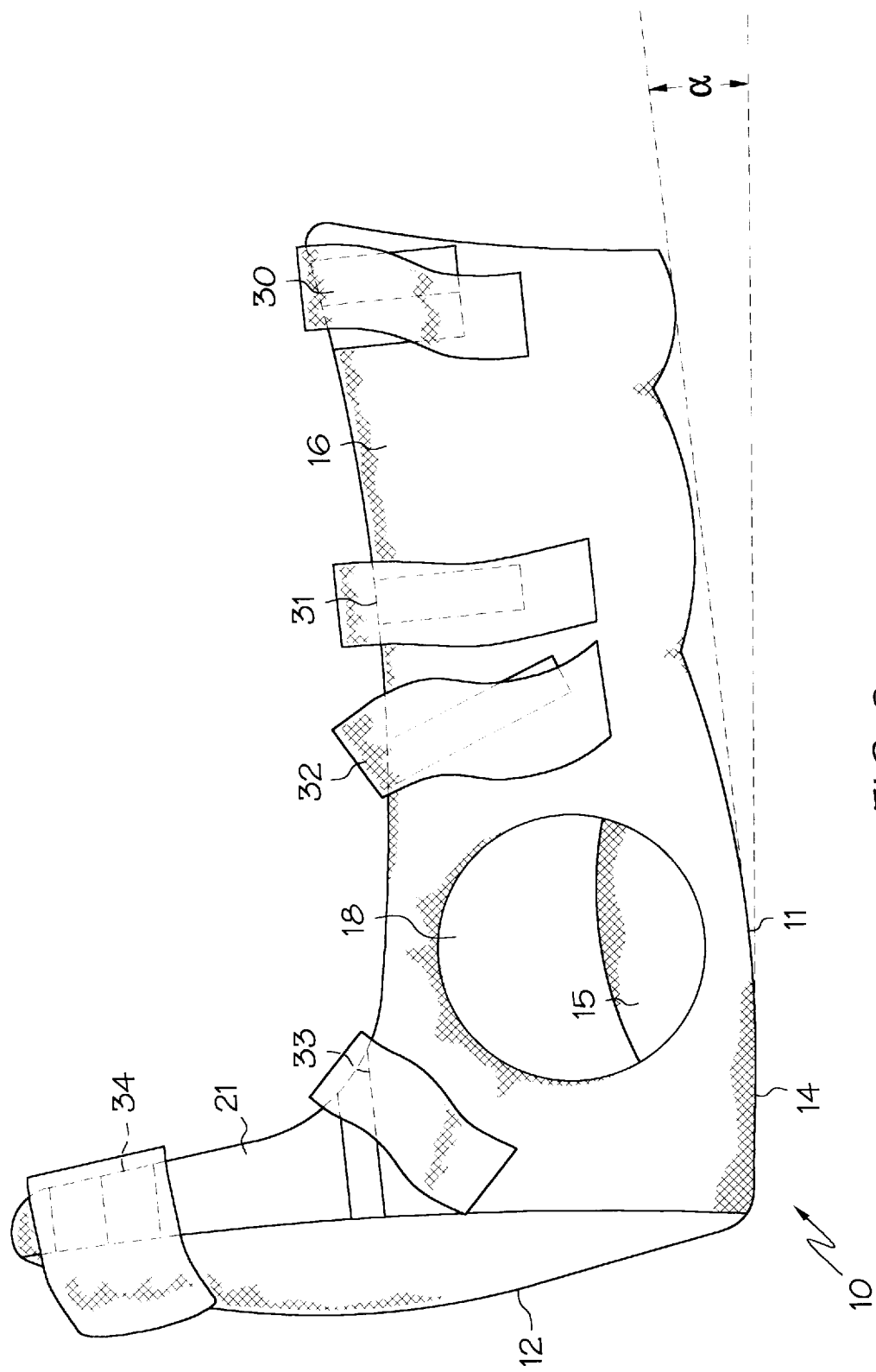
FIG. 2 is a side elevational view of the orthotic cushioned article of FIG. 1.

As best seen in FIG. 2, the leg portion 11 and the foot portion 12 of the orthotic cushioned article 10 extend from one another at substantial right angles to form the generally L-shaped configuration. As depicted, the leg portion 11 is longer than the foot portion 12. The leg portion can as well be the same length or shorter than the foot portion depending on design choices dictated by the intended individual's age and body part development and also the particular physical ailment being treated. Typically, the leg portion 11 ranges from about five inches to about fifteen inches in length and the foot portion ranges from about three inches to about twelve inches in length. Preferably, the article has a leg portion longer than the foot portion to increase its capability of being used on several individuals with varied needs. Such preferred cushioned orthotic articles have a leg portion of from about ten inches to about fifteen inches and a foot portion of from about eight inches to about ten inches.

Still with reference to FIG. 2, the leg portion 11 of the orthotic cushioned article 10 when placed on a horizontal surface such as a bed in a use position is shaped so as to be gradually inclined upwardly towards the individual's knee.

A built-up supportive section 14 in a lower extremity of the leg portion 11 is ideally used for this purpose. An angle of inclination of preferably about fifteen degrees to about twenty degrees from the horizontal allows the article to be used in a manner which approximates the natural position of the individual's leg when lying on his or her back. That is, the article's configuration allows the foot to be held in proper anatomical alignment. The prescribed angle of inclination avoids knee hyperextension, prevents foot drop and prevents achilles tendon shortening. These are all conditions which can result from being in bed for a prolonged time.

Figure 3:
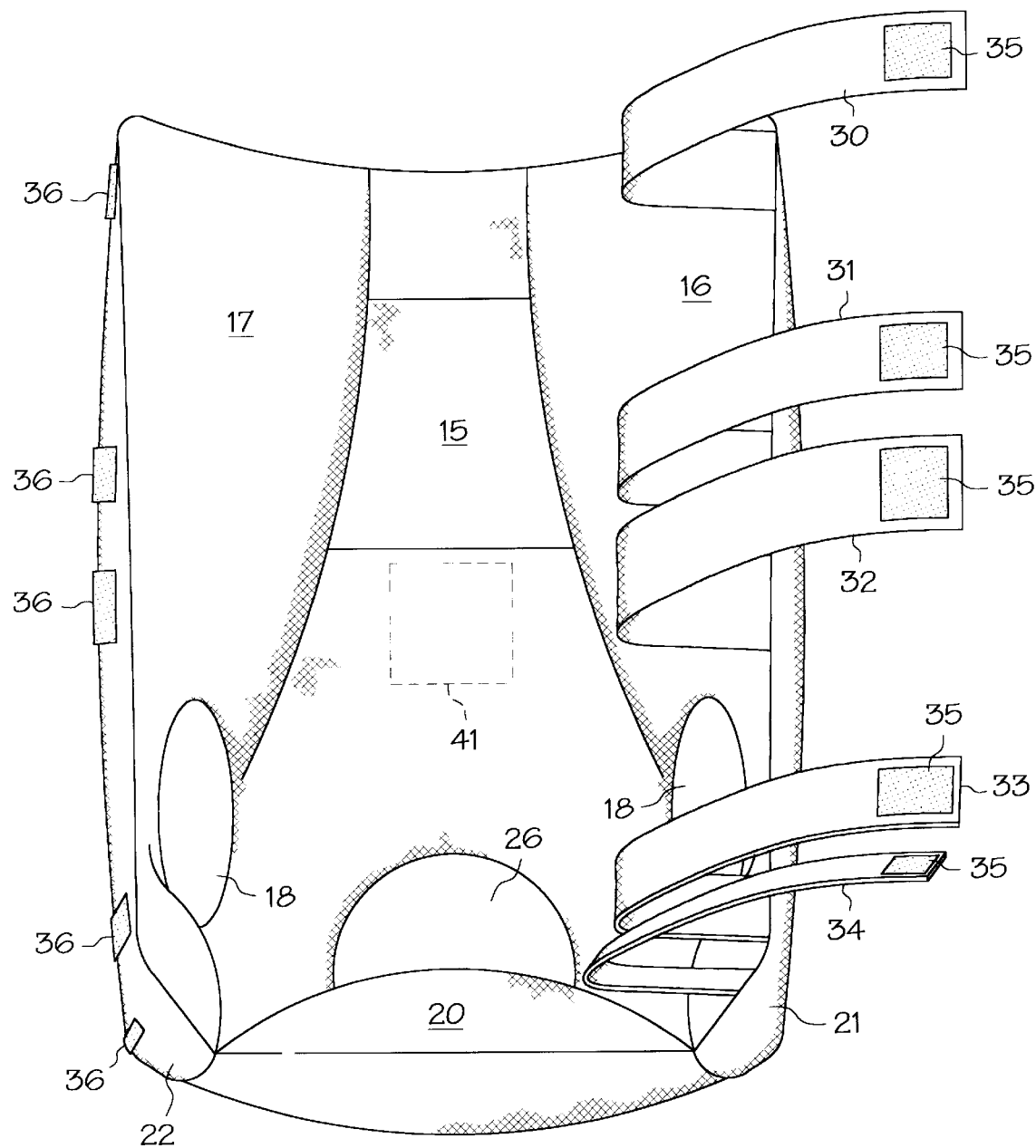
FIG. 3 is a top plan view of the orthotic cushioned article of FIG. 1.
Figure 4:
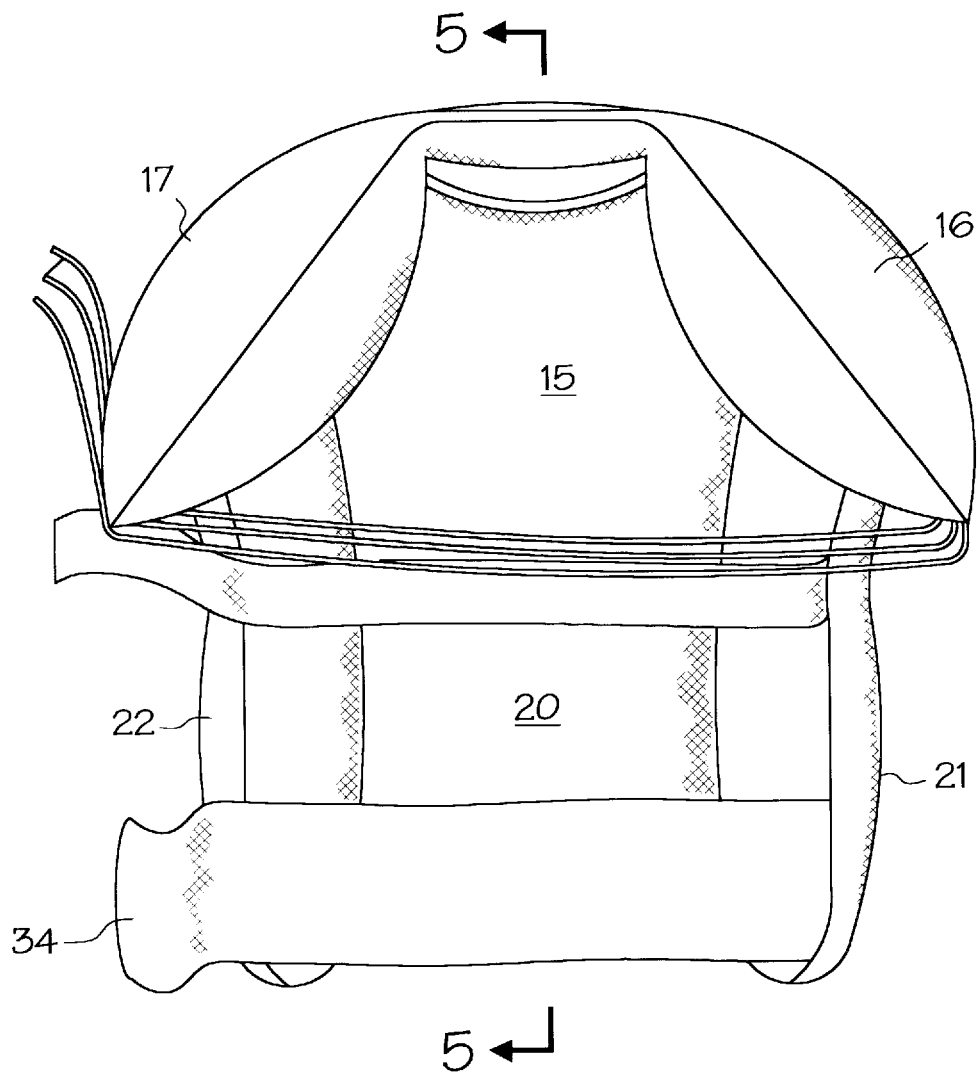
FIG. 4 is an end elevational view of the orthotic cushioned article of FIG. 1.

The leg portion 11 of the article, as best seen in FIGS. 3 and 4 has a flattened centerwall 15, a first sidewall 16 extending upwardly from the centerwall and a second sidewall 17 extending upwardly from an opposite side of the centerwall. The sidewalls 16 and 17 create a channel to receive the lower leg of the individual. As evident in FIGS. 1–3, each sidewall 16 and 17 has a cut-out 18 near a lower extremity to accommodate the ankle bone of the individual. One cut-out accommodates the outer ankle bone and the other cut-out accommodates the inner ankle bone. They can be any shape, though a circular shape is preferred for manufacturing reasons. The cut-outs are preferably about three inches to about four inches in diameter. They allow the ankle bone to extend into them without contact by the article itself and, because of the article's configuration and cushioned nature, without contact of a bed surface or similar abrasive surface.

The foot portion 12 also has a flattened centerwall 20 and preferably a first sidewall 21 and a second sidewall 22 extending upwardly. A junction of the leg portion 11 and foot portion 12 has an approximately centered cut-out 26 to accommodate the individual's heel bone. The heel is thus freely supported in the cut-out 26 without pressure. The cut-out 26 is preferably circular-shaped and about two inches to about four inches in diameter.

The leg portion 11 and the foot portion 12 of the article 10 are both cushioned. Preferably, each portion has a soft flexible surface covering and a soft yieldable material within the surface covering for comfort reasons. The surface covering can be a one piece casing, though more typically is several pieces sewn or otherwise held together to create a casing to hold the soft yieldable material. Coverings include natural and synthetic woven or non-woven films and fabrics. A highly preferred covering is a soft vinyl sheet-like material for cleaning, durability and manufacturing reasons. Examples of soft yieldable materials include cotton, wool and synthetic materials in the form of pads, mats and battings. Another example is a synthetic foam. The foam is highly preferred primarily because of its inherent light weight. As a result, the full article is light weight and is much more conducive to the individual being able to do routine leg and foot exercises while wearing the article. This is important in that the individual can do such exercises at leisure without having to remove the article.

As most evident in FIG. 1, the orthotic cushioned article 10 has securing means 13 for releasably holding the article to the individual for an extended recuperative time period, e.g. several days. A preferred securing means depicted in FIGS. 1–5 is a set of straps 30–34. Three separate straps 30–32 are on the leg portion and two separate straps 33 and 34 are on the foot portion 12. The straps all have a length sufficiently long to reach across the top of the channels in the leg and foot portions. Each of the straps is preferably substantially equi-spaced from one another. The straps are permanently sewn at one end into the article at a top of one sidewall. A free-end of each strap has a hook and loop fastener patch 35 on its underside and mates with a hook or loop fastener patch 36 permanently attached at or near a top of another sidewall and in alignment therewith. As evident in FIGS. 1, 2, 4 and 5, the strap 34 is wider than the other straps to spread a holding force over a wider area and lessen the likelihood of irritating tops of the individual's toes.

The free-ends of the straps 30–34 are easily pulled away from the article and then the individual's lower leg and foot placed in the channels of the article. The free-ends of the straps are repositioned over the leg and foot and mated with the hook and loop fastener patches to loosely, though securely, hold the article in place.

Other securing means can be used to hold the cushioned orthotic article to the individual. For example, adhesive tape, belts, drawstrings, and laces can be used.

Figure 5:
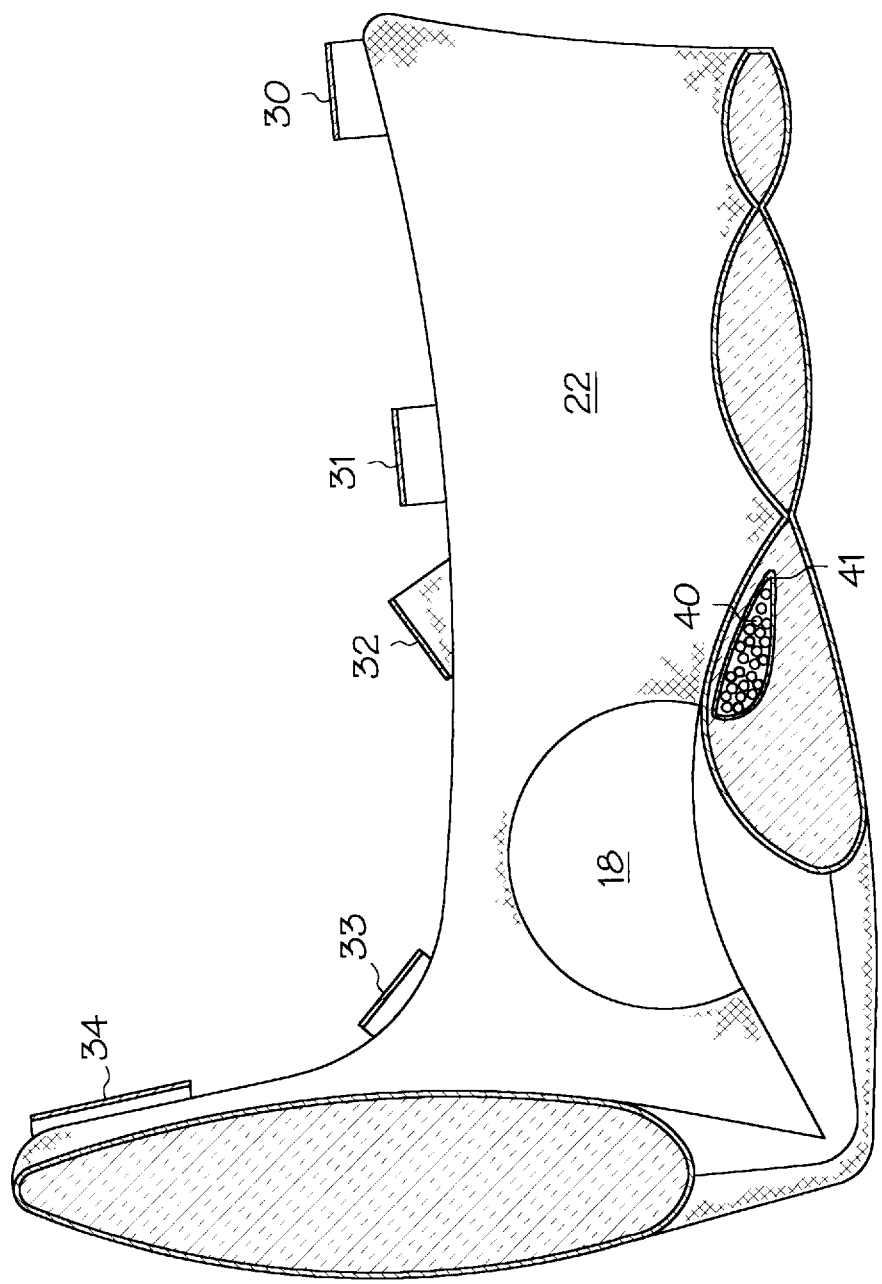
FIG. 5 is a side elevational view taken in section of the orthotic cushioned article of FIG. 1 taken along line 5—5 of FIG. 4.

With reference to FIGS. 3–5, a set of beads 40 are positioned in at least the leg portion 11 of the orthotic cushioned article 10 to enhance superficial blood circulation. The beads 40 are in the flattened centerwall 15 of the leg portion 11 just below the surface of the covering. As shown, the beads are positioned to contact the individual's leg just above the achilles tendon when the article is used. Preferably, they are contained within a packet 41 and the packet 41 is held in place by stitching. The beads 40 are about 100 mils to about 400 mils diameter hard spherical-shaped objects. They can be made of natural or synthetic material such as a plastic. Preferably, they are made of an odor sorbing synthetic polymeric material.

The article acts as a foot prop to keep the individual's ankle and heel bone off the bed surface. The ankle and heel bones are free from any substantial contact with an abrasive surface of any nature. Aeration of the foot is provided by the structural openings of the article. The cushioned nature of the article provides the foot comfort needed and expected. Its light weight allows foot and leg exercises which can aid in any healing. Most importantly, the article has a therapeutic effect due to inclusion of the beads and enhanced superficial blood circulation. Adverse side effects such as knee hyperextension, foot drop and achilles tendon shortening so common with many foot props are avoided because of the cushioned orthotic article's configuration. The preferred vinyl surface covering also contributes to the products desirability because of its easy cleanability.

In use, the securing means are released from the orthotic cushioned article of the invention and the article placed under the leg of the bed-ridden individual. The article is placed so that the individual's outer and inner ankle bones extend into the cut-outs of the leg portion and the heel extends into the junction cut-out. The securing means are then used to hold the cushioned article to the individual. The article can be left in place for several hours. Superficial blood circulation is simulated when the individual even slightly moves the leg within the article. Normal and needed leg movements can occur without undue effort on the part of the individual. Periodically, the article can be removed, cleaned and replaced. The formation of decubital ulcers is noticeably lessened and existing decubital ulcers alleviated.

Optionally, the cushioned orthotic article of the invention can have other various features to enhance its use. For example, strategically located water or air pockets provide pressure relief.

Having described the invention in its preferred embodiment, it should be clear that modifications can be made without departing from the spirit of the invention. It is not intended that the words used to describe the invention nor the drawings illustrating the same be limiting on the invention. It is intended that the invention only be limited by the scope of the appended claims.

I claim:

1. An orthotic cushioned article for supporting the foot and ankle of an individual in an inclined position for an extended recuperative time period without the formation of decubital ulcers, said cushioned article having a generally L-shaped configuration to follow the contour of the individual's lower leg and foot with (i) a leg portion having a flattened centerwall with a first sidewall extending upwardly from the centerwall and a second sidewall extending upwardly from the centerwall such that the flattened centerwall, first sidewall and second sidewall partially encompass the leg and (ii) a foot portion with a centerwall extending at a substantially right angle from the centerwall of the leg portion, further wherein each of the leg portion sidewalls has a cut-out to accommodate the ankle of the individual and a junction of the leg portion centerwall and foot portion centerwall has a cut-out to accommodate the heel of the individual, said cushioned article still further having beads disposed in at least the centerwall of the leg portion to enhance blood circulation and having securing means to releasably hold the cushioned orthotic article to the individual in a manner whereby the ankle and heel bones of the individual are suspended without surface contact.

2. The orthotic cushioned article of claim 1 wherein the securing means are a set of straps permanently secured to the first sidewall of the leg portion, wherein a free-end of each strap has a hook or loop fastener patch attached to an underside and a mating and aligned hook or loop fastener patch is permanently secured to the second side wall of the leg portion.

3. The orthotic cushioned article of claim 1 wherein the beads are contained within a packet.

4. The orthotic cushioned article of claim 3 wherein the beads have a diameter of from about 100 mils to about 400 mils.

5. The orthotic cushioned article of claim 1 wherein the leg portion has greater length than the foot portion.

6. The orthotic cushioned article of claim 5 wherein the leg portion has a length of from about five inches to about fifteen inches and the foot portion has a length of from about three inches to about twelve inches.

7. The orthotic cushioned article of claim 6 wherein the ankle cut-outs in the leg portion are circular-shaped and have a diameter of from about three inches to about four inches.

8. The orthotic cushioned article of claim 7 wherein the heel cut-out at the junction of the leg portion and foot portion is circular-shaped and has a diameter of from about two inches to about four inches.

9. The orthotic cushioned article of claim 1 wherein the leg portion and the foot portion are casings of a soft vinyl surface covering and each has a yieldable material contained therewithin.

10. The orthotic cushioned article of claim 1 wherein the leg portion is configured to have an upward angle of inclination to the horizontal.

11. The orthotic cushioned article of claim 1 wherein the leg portion has an angle of inclination from the horizontal of from about fifteen degrees to about twenty degrees.

12. An orthotic cushioned article for supporting the foot and ankle of an individual in an inclined position for an extended recuperative time period without the formation of decubital ulcers, said cushioned article having a generally L-shaped configuration to follow the contour of the individual's lower leg and foot with (i) a leg portion having a flattened centerwall with a first sidewall extending upwardly from the centerwall and a second sidewall extending upwardly from the centerwall such that the flattened centerwall, first sidewall and second sidewall partially encompass the leg and further configured to have an upward angle of inclination of from about fifteen degrees to about twenty degrees from the horizontal and (ii) a foot portion with a centerwall extending at a substantially right angle from the centerwall of the leg portion, further wherein each of the leg portion sidewalls has a cut-out to accommodate the ankle of the individual and a junction of the leg portion centerwall and foot portion centerwall has a cut-out to accommodate the heel of the individual, said cushioned article still further having synthetic polymeric odor sorbing beads disposed in at least the centerwall of the leg portion to enhance blood circulation and strap securing means to releasably hold the cushioned orthotic article to the individual in a manner whereby the ankle and heel bones of the individual are suspended without surface contact.

13. The orthotic cushioned article of claim 12 wherein the strap securing means have hook and loop fastener patches to attach to one another.

14. The orthotic cushioned article of claim 12 wherein the beads are contained within a packet and the packet is positioned in the centerwall of the leg portion above the individual's achilles tendon when the article is used.

15. The orthotic cushioned article of claim 14 wherein the beads have a diameter of from about 100 mils to about 400 mils.

16. The orthotic cushioned article of claim 14 wherein the leg portion has greater length than the foot portion.

* * * * *